United States Patent [19]

Ishibashi

[11] 4,107,291
[45] Aug. 15, 1978

[54] COMPOSITIONS FOR CLEANING TEETH AND ORAL CAVITY

[75] Inventor: Keijiro Ishibashi, Tokyo, Japan

[73] Assignee: Sankyo Company Limited, Tokyo, Japan

[21] Appl. No.: 237,577

[22] Filed: Mar. 23, 1972

Related U.S. Application Data

[63] Continuation of Ser. No. 43,224, Jun. 3, 1970, abandoned.

[30] Foreign Application Priority Data

Jun. 5, 1969 [JP] Japan .................................. 44-44210

[51] Int. Cl.² ........................... A61K 7/28; A61K 9/68
[52] U.S. Cl. ......................................... 424/48; 424/50
[58] Field of Search ...................................... 424/48-58

[56] References Cited

U.S. PATENT DOCUMENTS 3,733,399  5/1973  Becker et al. .......................... 424/50

FOREIGN PATENT DOCUMENTS 1,927,411  10/1970  Fed. Rep. of Germany.

OTHER PUBLICATIONS

U.S.P.T.O. Translation (6-21-77) of German OLS No. 1,927,411, Dec. 10, 1970, (filed May 28, 1969 by Bonse et al.), 12 pp.

*Primary Examiner*—Shep K. Rose
*Attorney, Agent, or Firm*—Flynn & Frishauf

[57] ABSTRACT

Compositions for cleaning teeth and oral cavity which contains as an active ingredient an effective amount of invertase. The present cleaning composition is especially effective in reduction of dental plaque formation and prevention of dental caries.

24 Claims, No Drawings

COMPOSITIONS FOR CLEANING TEETH AND ORAL CAVITY

This is a continuation, of application Ser. No. 43,224, filed June 3, 1970, now abandoned.

This invention relates to a composition for cleaning teeth and oral cavity and also to a method for cleaning such tissue and organ.

More particularly, it is concerned with a composition for cleaning teeth and oral cavity, especially diminishing the formation of dental plaque and preventing dental caries, which contains as an active ingredient an effective amount of invertase and also with a method for cleaning such tissue and organ.

Presently, the reason why dental caries would be formed is believed due to the fact that carbohydrates in food residue remaining between interspaces of teeth and also in the pits and fissures of teeth tend to be decomposed by the action of acid-producing bacteria into lactic acid, which may promote decalcification of dental tissues, thereby leading to the formation of dental caries. It is also known that such acid-producing bacteria firmly adhere upon the surface of tooth as a film of very thin bacterial plaque to form dental plaque. Further, it is found in the art that one of the constituents of dental plaque is identified with dextran, which plays a great role in the formation and adhesion of dental plaque.

As discussed above, there is a close relationship between the formation of dental caries and dental plaque and then it is believed useful for eliminating or diminishing cariogenic factors to prevent the formation and adhesion of dental plaque. Accordingly, it is significant in view of oral hygiene and desired in the art to develop an effective means for such a purpose.

Now, it has been unexpectedly found that a certain enzyme, invertase, exerts a prominent biological activity in diminishing the formation of dental plaque in oral cavity and this invention has been completed based upon this finding.

Accordingly, it is an object of this invention to provide a composition for cleaning teeth and oral cavity which contains as an active ingredient an effective amount of invertase.

It is another object of this invention to provide a method for cleaning teeth and oral cavity which comprises applying a sufficient amount of invertase to exert the aforesaid cleaning effect to teeth and oral cavity.

These and other objects of this invention will be apparent from the following detailed description of this invention.

The enzyme which may be employed as an active ingredient in this invention, invertase, is known as such and can be readily available from a wide variety of yeasts, e.g. bakers yeast, beer yeast and the like by a conventional method, for example, according to the teachings in "Methods in Enzymology", vol. 1, pages 252-255, edited by S. P. Colowick and N. O. Kaplan, Academic Press Inc. Publishers, N.Y., 1955. Commercially available invertase may, of course, be employed in this invention, if desired, after further purification. In any case, it is desirable in this invention to select and employ a purified form of almost tasteless and highly stable invertase.

According to this invention, the active enzyme may be usually employed and applied in various types of oral compositions or preparations having an effective amount of the enzyme incorporated therein. Suitable examples of these compositions are tooth pastes, powders and washes, troches, chewing gums, gargarisma and various types of oral preparations for spreading on teeth, e.g. ointments and lotions. The composition of this invention may usually contain the active enzyme in an effective amount, i.e. 10-3,000 units of invertase per gram of the composition with about 200 units/g. being preferable. The remainder of the composition of this invention may be optionally composed of any of those orally acceptable excipients commonly utilized in the art for such a purpose. Although it is to be understood that a prolonged time of the cleaning action is desirable in oral cavity, better results may be achieved by modification of an application method and optional increase in the number of times to be applied for a long duration of the cleaning action.

The mechanism or system of the present cleaning action has not been fully understood, but it is reasonably believed that invertase has an action to decompose and invert the sucrose remaining in oral cavity such as interspaces of teeth and so on, whereby the formation of dextran, which at least partly constitutes dental plaque, may be effectively prevented and consequently the formation of dental plaque and its adhesion to teeth may be diminished or eliminated.

The activity unit of invertase as used herein is defined as an amount of enzyme which liberates 1 mg. of glucose in 1 minute when the enzyme is subjected to a reaction with 0.5 g. (1.46 millimoles) of sucrose in 5 ml. of 0.05 mole acetate buffer (pH 5.0) at 30° C.

The following examples are given for the purpose of illustration of this invention. However, they should not be construed to be limiting the scope of this invention. In these examples, percentages are given by weight unless otherwise indicated.

EXAMPLE 1

Into the tooth powder having the following composition was incorporated invertase in an amount of 200 units per gram of the powder and the mixture was uniformly blended to form the invertase-containing tooth powder.

| | | |
|---|---|---|
| Precipitated calcium carbonate | 74 | % |
| Dibasic calcium phosphate | 15 | % |
| Glycerol | 10 | % |
| Sodium lauryl sulfate | 2.5 | % |
| Essential oil | 2.2 | % |
| Saccharin | 0.3 | % |

EXAMPLE 2

Into the tooth paste having the following composition was incorporated invertase in an amount of 200 units per gram of the paste and the mixture was uniformly blended to form the invertase-containing tooth paste.

| | | |
|---|---|---|
| Dibasic calcium phosphate | 50 | % |
| Glycerol | 20 | % |
| Sodium lauryl sulfate | 2.5 | % |
| Spearmint oil | 2.5 | % |
| Tragacanth gum | 1.0 | % |
| Saccharin | 0.1 | % |
| Water | 24.9 | % |

EXAMPLE 3

Into the tooth wash having the following composition was incorporated invertase in an amount of 200 units per gram of the wash and the mixture was uniformly blended to form the invertase-containing tooth wash.

| | | |
|---|---|---|
| Sodium carboxymethyl cellulose | 4.0 | % |
| Sodium lauryl sulfate | 2.0 | % |
| Glycerol | 30 | % |
| Perfume (spearmint oil and cinnamon oil, 1:1) | 0.5 | % |
| Water | 63.5 | % |

EXAMPLE 4

Into the chewing gum base having the following composition was incorporated invertase in an amount of 400 units per gram of the gum and the mixture was uniformly blended to form the invertase-containing chewing gum.

| | |
|---|---|
| Polyvinyl acetate | 20 % |
| Butyl phthalylbutylglycolate | 3 % |
| Polyisobutylene | 3 % |
| Microcrystalline wax | 2 % |
| Calcium carbonate | 2 % |
| Glucose | 69 % |
| Perfume (spearmint oil and cinnamon oil, 1:1) | 1 % |

EXAMPLE 5

The same procedure as in Example 1 was repeated except that the invertase was employed in an amount of 10 units per gram of the powder instead of 200 units per gram of the powder to form the invertase-containing tooth powder.

EXAMPLE 6

The same procedure as in Example 2 was repeated except that the invertase was employed in an amount of 10 units per gram of the paste instead of 200 units per gram of the paste to form the invertase-containing tooth paste.

EXAMPLE 7

The same procedure as in Example 3 was repeated except that the invertase was employed in amount of 10 units per gram of the wash instead of 200 units per gram of the wash to form the invertase-containing tooth wash.

EXAMPLE 8

The same procedure as in Example 4 was repeated except that the invertase was employed in an amount of 10 units per gram of the gum base instead of 200 units per gram of the gum base to form the invertase-containing chewing gum.

EXAMPLE 9

Into the gargarisma having the following composition was incorporated invertase in an amount of 100 units per gram of the gargarisma and the mixture was uniformly blended to form the invertase-containing gargarisma.

| | | |
|---|---|---|
| Glycerol | 50 | % |

| -continued | | |
|---|---|---|
| Perfume (spearmint oil and cinnamon oil, 1:1) | 0.5 | % |
| Water | 49.5 | % |

The resulting gargarisma is, when applied, diluted with water to the 10 times volume thereof.

EXAMPLE 10

Into a commercially available lotion or ointment for tooth was incorporated invertase in an amount of 3,000 units per gram of the lotion or ointment to form the invertase-containing lotion or ointment for tooth.

What is claimed is:

1. A method for cleaning teeth and oral cavity which comprises applying a sufficient amount of invertase to exert said cleaning effect to teeth and oral cavity.

2. The method according to claim 1, wherein the invertase is employed in the form of a composition containing 10 – 3,000 units thereof per gram of the composition.

3. The method according to claim 2, wherein said composition is in the form of a tooth powder.

4. The method according to claim 2, wherein said composition is in the form of a tooth paste.

5. The method according to claim 2, wherein said composition is in the form of a gargarisma.

6. The method according to claim 2, wherein said composition is in the form of an ointment for teeth.

7. The method according to claim 2, wherein said composition is in the form of a lotion for teeth.

8. The method according to claim 2, wherein said composition is in the form of a chewing gum.

9. A composition for cleaning teeth and oral cavity which comprises as an active ingredient invertase in a sufficient amount to exert said cleaning effect and a conventional orally acceptable excipient for teeth and oral cavity, said amount being 10 – 3000 units of the enzyme per gram of the composition.

10. The composition according to claim 9, wherein said composition is in the form of a tooth powder.

11. The composition according to claim 9, wherein said composition is in the form of a tooth paste.

12. The composition according to claim 9, wherein said composition is in the form of a tooth wash.

13. The composition according to claim 9, wherein said composition is in the form of a gargarisma.

14. The composition according to claim 9, wherein said composition is in the form of an ointment for teeth.

15. The composition according to claim 9, wherein said composition is in the form of a lotion for teeth.

16. The composition according to claim 9, wherein said composition is in the form of a chewing gum.

17. A toothpaste preparation comprising dibasic calcium phosphate, water and from 10 to 3000 units of invertase.

18. The toothpaste preparation claimed in claim 17, wherein said invertase is the sole active enzyme and is present in a pure state.

19. The toothpaste preparation claimed in claim 17, wherein said phosphate is present in an amount of about 50% by weight.

20. The toothpaste preparation claimed in claim 19, wherein water is present in an amount of about 25% by weight and said preparation also contains about 1% by weight of tragacanth gum and about 2.5% by weight of sodium lauryl sulfate.

21. A toothpaste preparation comprising dibasic calcium phosphate, water, and 200 units of invertase per gram of the preparation.

22. The toothpaste preparation of claim 21, wherein said invertase is the sole active enzyme and is present in a pure state.

23. The toothpaste preparation claimed in claim 21, wherein said phosphate is present in an amount of 50% by weight.

24. The toothpaste preparation claimed in claim 23, wherein said water is present in an amount of about 25% by weight and said preparation also contains about 1.0% by weight of tragacanth gum and about 2.5% by weight of sodium lauryl sulfate.

* * * * *